(12) United States Patent
Dyballa et al.

(10) Patent No.: US 9,896,404 B2
(45) Date of Patent: *Feb. 20, 2018

(54) BIDENTATE DIPHOSPHORAMIDITES WITH A HOMOPIPERAZINE GROUP AS LIGANDS FOR HYDROFORMYLATION

(71) Applicant: EVONIK DEGUSSA GMBH, Essen (DE)

(72) Inventors: Katrin Marie Dyballa, Recklinghausen (DE); Robert Franke, Marl (DE); Dirk Fridag, Haltern am See (DE); Dieter Hess, Marl (DE); Frank Geilen, Haltern am See (DE); Galina Morales Torres, Rostock (DE); Detlef Selent, Rostock (DE); Armin Börner, Rostock (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/381,765

(22) Filed: Dec. 16, 2016

(65) Prior Publication Data

US 2017/0174601 A1    Jun. 22, 2017

(30) Foreign Application Priority Data

Dec. 21, 2015   (EP) .................... 15201654

(51) Int. Cl.
| | |
|---|---|
| C07C 45/50 | (2006.01) |
| C07F 15/00 | (2006.01) |
| C07F 9/6571 | (2006.01) |
| C07F 9/645 | (2006.01) |
| B01J 31/18 | (2006.01) |

(52) U.S. Cl.
CPC ............. *C07C 45/50* (2013.01); *B01J 31/186* (2013.01); *C07F 9/645* (2013.01); *C07F 9/657154* (2013.01); *C07F 15/008* (2013.01); *B01J 2231/321* (2013.01); *B01J 2531/0205* (2013.01); *B01J 2531/822* (2013.01)

(58) Field of Classification Search
CPC ...... C07C 45/50; C07C 45/505; B01J 31/186; C07F 9/645; C07F 9/657163
USPC ................................ 568/454, 455
See application file for complete search history.

(56) References Cited

U.S. PATENT DOCUMENTS

| | | |
|---|---|---|
| 4,739,000 A | 4/1988 | Burton |
| 2008/0207942 A1 | 8/2008 | Reetz et al. |
| 2016/0152539 A1 | 6/2016 | Dyballa et al. |

FOREIGN PATENT DOCUMENTS

| | | |
|---|---|---|
| WO | 2007/031065 A1 | 3/2007 |
| WO | 2015/011145 A1 | 1/2015 |
| WO | 2016/020199 A1 | 2/2016 |
| WO | 2016/034327 A1 | 3/2016 |
| WO | 2016/034328 A1 | 3/2016 |
| WO | 2016/034330 A1 | 3/2016 |

OTHER PUBLICATIONS

Mazuela et al. Fine-tunable rnonodentate phosphoroamidite and aminophosphine ligands for Rh-catalyzed asymmetric hydroformylation, Tetrahedron Asymmetry. 2010, 21. 2153-2157.
Van Rooy et al, Phosphoramidites: novel modifying ligands in rhodium catalyzed hydroformylation, Recl. Trav. Chim. Pays-Bas 1996, 115, 492-498.
Yan et al. A Hybrid Phosphorus Ligand for Highly Enantioseleetive Asymmetric Hydroformylation. J. Am. Chem. Soc. 2006, 128, 7198-7202.
Hua et al. New biphenol-based, fine-tunable monodentate phosphoramidite ligands for catalytic asymmetric transformations. PNAS, 2004, 101, No. 14, 5411-5416.
Sheldrick, G. M. A short history of SHELX. Acta. Crystallographica A64, 2008, 112-122.
Sheldrick, G. M. Crystal structure refinement with SHELXL, Acta. Crystallographica, C71, 2015, 3-8.
Benetskiy et al. Rhodium-Catalyzed Nonisomerizing Hydroformylation of Methyl Oleate Applying Lactame-Based Phosphoramidite Ligands. ACS Catal., 2014, 4, 2130-2136.
Tsarev et al. Complexing and catalytic properties of easily available chiral iminophosphite based on biphenyl-2,2'-diol. Russian Chemical Bulletin, Int. Ed. 2004, vol. 53, 814-818.
Frank et al. Asymmetric Hydrogenation Using Rhodium Complexes Generated from Mixtures of Monodentate Neutral and Anionic Phosphorus Ligands. Chem. Eur. J., 2013, 19, 2405-2415.
Lot et al. New electron-deficient aminophosphonite-phosphite ligands for asymmetric hydroformylation of styrene. J. Mol. Catal. A: Chem. 164, 2000, 125-130.
Feringa et al. Phosphoramidites: Privileged Ligands in Asymmetric Catalysis. Angew. Chem. Int. Ed. 49, 2010, 2486-2528.
Balaraman et al. A convenient chromatography-free access to enantiopure 6,60-di-tert-butyl-1,10-binaphthalene-2,20-diol and its 3,30-dibromo, di-tert-butyl and phosphorus derivatives: utility in asymmetric synthesis, Tetrahedron: Asymmetry 18, 2007, 2037-2048.
Rodriguez i Zubiri et al. The preparation and coordination chemistry of phosphorus(III) derivatives of piperazine and homopiperazine, Polyhedron. 21, 2002, 1729-4736.

(Continued)

*Primary Examiner* — Sikarl Witherspoon
(74) *Attorney, Agent, or Firm* — Smith, Gambrell & Russell, LLP

(57) ABSTRACT

The invention relates to Rh, Ru, Co and Ir complexes comprising bidentate diphosphoramidites as ligands and to the use thereof as catalysts for the hydroformylation of olefins. The invention also relates to a process for preparing an aldehyde from an olefin using the complexes or ligands mentioned.

18 Claims, No Drawings

(56) References Cited

OTHER PUBLICATIONS

Choi et al. Copper-catalyzed conjugate addition on macrocyclic, cyclic, and acyclic enones with a chiral phosphoramidite ligand having a $C_2$-symmetric amine moiety. Tetrahedron: Asymmetry. 13, 2002, 801-804.
Vuagnoux-d'Augustin et al. Copper-Catalyzed Asymmetric Conjugate Addition of Trialkylaluminium, Reagents to Trisubstituted Enones: Construction of Chiral Quaternary Centers. Chem. Eur. J, 13, 2007, 9647-9662.
Lühr et al. The Synthesis of Chiral Phosphorus Ligands for use in Homogeneous, Metal Catalysis. ChemCatChem, 3, 2011, 1708-1730.
International Search Report for EP 15 20 1654 dated May 23, 2016 (1 page).
Franke, R., Selent, D., and Börner, A. Applied Hydroformylation. American Chemical Society, ACS Publications, Chemical Reviews, 2012. pp. 5675-5732.
B. Cornils, W. A. Herrmann, Applied Homogeneous Catalysis with Organometallic Compounds, vol. 1 & 2, VCH, Weinheim, New York, 1996. Forward, Preface and Table of Contents provided.

BIDENTATE DIPHOSPHORAMIDITES WITH A HOMOPIPERAZINE GROUP AS LIGANDS FOR HYDROFORMYLATION

The invention relates to Rh, Ru, Co and Ir complexes comprising bidentate diphosphoramidites as ligands and to the use thereof as catalysts for the hydroformylation of olefins. The invention also relates to a process for preparing an aldehyde from an olefin using the complexes or ligands mentioned.

The reactions between olefin compounds, carbon monoxide and hydrogen in the presence of a catalyst to give the aldehydes comprising one additional carbon atom are known as hydroformylation or oxo synthesis. In terms of volume, hydroformylation is one of the most important homogeneous catalyses on the industrial scale. The aldehydes obtained are important intermediates or end products in the chemical industry (B. Cornelis, W. A. Herrmann, "Applied Homogeneous catalysis with organometallic compounds", Vol. 1 & 2, VCH, Weinheim, N.Y., 1996; R. Franke, D. Selent, A. Börner, Chem. Rev. 2012, 112, 5675).

The catalysts used in hydroformylation are frequently compounds of the transition metals of group VIII of the Periodic Table of the Elements. Of particular significance here are Rh catalysts. The catalysts further comprise suitable ligands, for example compounds from the classes of the phosphines, phosphites and phosphonites, each with trivalent phosphorus. These trivalent phosphorus compounds are usually used to control activity and regioselectivity of the catalyst. Since the hydroformylation, except in the case of ethylene as reactant, leads to a mixture of isomeric products, namely n-aldehydes (linear aldehydes) and iso-aldehydes (branched aldehydes), aside from the reaction rate and hence yields, the selectivity in the formation of n and iso products is a particularly crucial parameter in the hydroformylation reaction.

Phosphoramidites, i.e. compounds having one or more P—N bonds rather than a P—O bond, have to date been used only rarely as ligands in hydroformylation.

Phosphoramidites having a phenyl-phenyl unit have been described in the literature (J. Mazuela et al., Tetrahedron Asymmetry, 2010, 21(17):2153-2157, page 2154, compound L2). Van Leeuwen and coworkers were the first to study monodentate phosphoramidites in hydroformylation (A. van Rooy, D. Burgers, P. C. J. Kamer, P. W. N. M. van Leeuwen, Recl. Tray. Chinn. Pays-Bas 1996, 115, 492). Overall, only moderate catalytic properties were observed at high ligand/rhodium ratios of up to 1000:1.

WO 2007/031065 A1 discloses the use of chiral phosphoramidites for asymmetric catalyses, but without citing working examples for hydroformylation.

Chiral bidentate ligands each having a phosphoramidite unit have been used in various forms in asymmetric hydroformylation (J. Mazuela, O. Pàrries, M. Diéguez, L. Palais, S. Rosset, A. Alexakis, Tetrahedron: Asymmetry 2010, 21, 2153-2157; Y. Yan, X. Zhang, J. Am. Chem. Soc. 2006, 128, 7198-7202; Z. Hua, V. C. Vassar, H. Choi, I. Ojima, PNAS 2004, 13, 5411-5416).

The problem addressed by the present invention is that of providing novel ligands and catalysts for hydroformylation, which assure a high yield and permit control of the n/iso ratio.

This problem is solved by compounds of one of the general formulae (I) and (II):

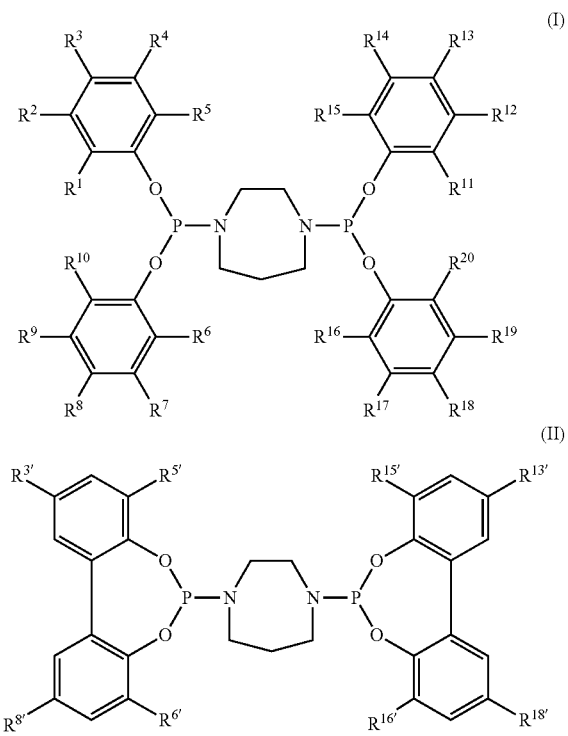

where $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl, halogen, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —OH, —N[$(C_1$-$C_{12})$-alkyl]$_2$;

and $R^{2'}, R^{3'}, R^{4'}, R^{5'}, R^{6'}, R^{7'}, R^{8'}, R^{9'}, R^{12'}, R^{13'}, R^{14'}, R^{15'}, R^{16'}, R^{17'}, R^{18'}, R^{19'}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl, halogen, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —OH, —N[$C_1$-$C_{12})$-alkyl]$_2$.

These compounds are a novel substance class which is especially suitable as ligands for Rh-, Ru-, Co- or Ir-catalysed hydroformylation of olefins.

$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}$ are preferably independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen.

In a preferred embodiment, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl.

In a particularly preferred embodiment, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{29}$ are independently selected from —H, —$(C_1$-$C_{12})$-alkyl, —O—$(C_1$-$C_{12})$-alkyl.

In a further particularly preferred embodiment, $R^1, R^2, R^3, R^4, R^5, R^6, R^7, R^8, R^9, R^{19}, R^{11}, R^{12}, R^{13}, R^{14}, R^{15}, R^{16}, R^{17}, R^{18}, R^{19}, R^{29}$ are independently selected from —H, —$(C_1$-$C_6)$-alkyl.

$R^{2'}, R^{3'}, R^{4'}, R^{5'}, R^{6'}, R^{7'}, R^{8'}, R^{9'}, R^{12'}, R^{13'}, R^{14'}, R^{15'}, R^{16'}, R^{17'}, R^{18'}, R^{19'}$ are preferably independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen.

In a preferred embodiment, $R^{2'}$, $R^{3'}$, $R^{4'}$, $R^{5'}$, $R^{6'}$, $R^{7'}$, $R^{8'}$, $R^{9'}$, $R^{12'}$, $R^{13'}$, $R^{14'}$, $R^{15'}$, $R^{16'}$, $R^{17'}$, $R^{18'}$, $R^{19'}$ are independently selected from —H, —($C_1$-$C_{12}$)-alkyl, —O—($C_1$-$C_{12}$)-alkyl, —($C_6$-$C_{20}$)-aryl, —O—($C_6$-$C_{20}$)-aryl.

In a particularly preferred embodiment, $R^{2'}$, $R^{3'}$, $R^{4'}$, $R^{5'}$, $R^{6'}$, $R^{7'}$, $R^{8'}$, $R^{9'}$, $R^{12'}$, $R^{13'}$, $R^{14'}$, $R^{15'}$, $R^{16'}$, $R^{17'}$, $R^{18'}$, $R^{19'}$ are independently selected from —H, —($C_1$-$C_{12}$)-alkyl, —O—($C_1$-$C_{12}$)-alkyl.

In a further particularly preferred embodiment, $R^{2'}$, $R^{3'}$, $R^{4'}$, $R^{5'}$, $R^{6'}$, $R^{7'}$, $R^{8'}$, $R^{9'}$, $R^{12'}$, $R^{13'}$, $R^{14'}$, $R^{15'}$, $R^{16'}$, $R^{17'}$, $R^{18'}$, $R^{19'}$ are independently selected from —H, —($C_1$-$C_6$)-alkyl.

In a further particularly preferred embodiment, $R^1$, $R^2$, $R^4$, $R^7$, $R^9$, $R^{10}$, $R^{11}$, $R^{12}$, $R^{14}$, $R^{17}$, $R^{19}$, $R^{20}$ are each H.

In a further particularly preferred embodiment, $R^{2'}$, $R^{4'}$, $R^{7'}$, $R^{9'}$, $R^{12'}$, $R^{14'}$, $R^{17'}$, $R^{19'}$ are each H.

In a further particularly preferred embodiment, the benzene or dibenzene rings of the compounds (I) and (II) are each substituted in the ortho and/or para positions.

In one embodiment, the compound has the general formula (I).

In a further embodiment, the compound has the general formula (II).

Particular preference is thus given to compounds of one of the formulae (III) or (IV):

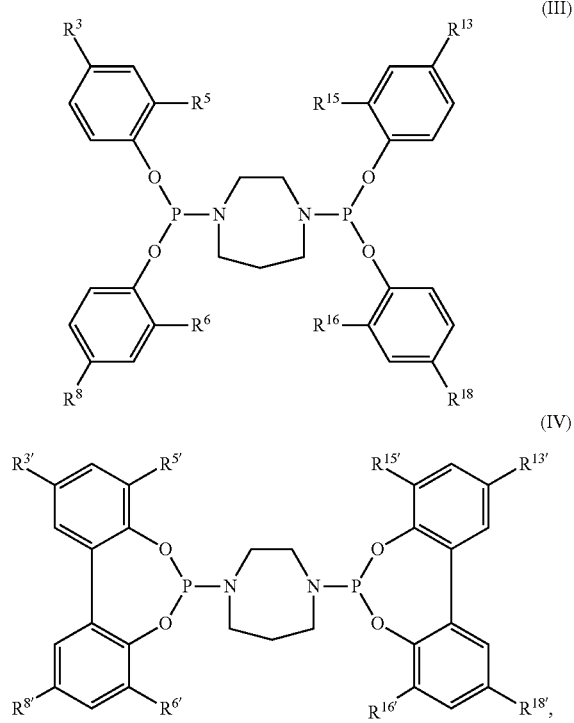

where $R^3$, $R^5$, $R^6$, $R^8$, $R^{13}$, $R^{15}$, $R^{16}$, $R^{18}$ are independently selected from —H, —($C_1$-$C_{12}$)-alkyl, —O—($C_1$-$C_{12}$)-alkyl, [—($C_6$-$C_{20}$)-aryl, —O—($C_6$-$C_{20}$)-aryl, halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —OH, —N[($C_1$-$C_{12}$)-alkyl]$_2$; and $R^{3'}$, $R^{5'}$, $R^{6'}$, $R^{8'}$, $R^{13'}$, $R^{15'}$, $R^{16'}$, $R^{18'}$ are independently selected from —H, —($C_1$-$C_{12}$)-alkyl, —O—($C_1$-$C_{12}$)-alkyl, —($C_6$-$C_{20}$)-aryl, —O—($C_6$-$C_{20}$)-aryl, halogen, —COO—($C_1$-$C_{12}$)-alkyl, —CONH—($C_1$-$C_{12}$)-alkyl, —CO—($C_1$-$C_{12}$)-alkyl, —CO—($C_6$-$C_{20}$)-aryl, —COOH, —OH, —N[($C_1$-$C_{12}$)-alkyl]$_2$.

More preferably, $R^3$, $R^5$, $R^6$, $R^8$, $R^{13}$, $R^{15}$, $R^{16}$, $R^{18}$ in this case are independently selected from —H, —($C_1$-$C_{12}$)-alkyl, —O—($C_1$-$C_{12}$)-alkyl.

More preferably, $R^{3'}$, $R^{5'}$, $R^{6'}$, $R^{8'}$, $R^{13'}$, $R^{15'}$, $R^{16'}$, $R^{18'}$ in this case are independently selected from —H, —($C_1$-$C_{12}$)-alkyl, —O—($C_1$-$C_{12}$)-alkyl.

In one embodiment, the compound has the general formula (III).

In a further embodiment, the compound has the general formula (IV).

It has been found that the following compounds (4) to (7) are particularly suitable ligands of the formulae (I) and (II). The complexes according to the invention therefore preferably comprise one of the compounds (4), (5), (6) and (7):

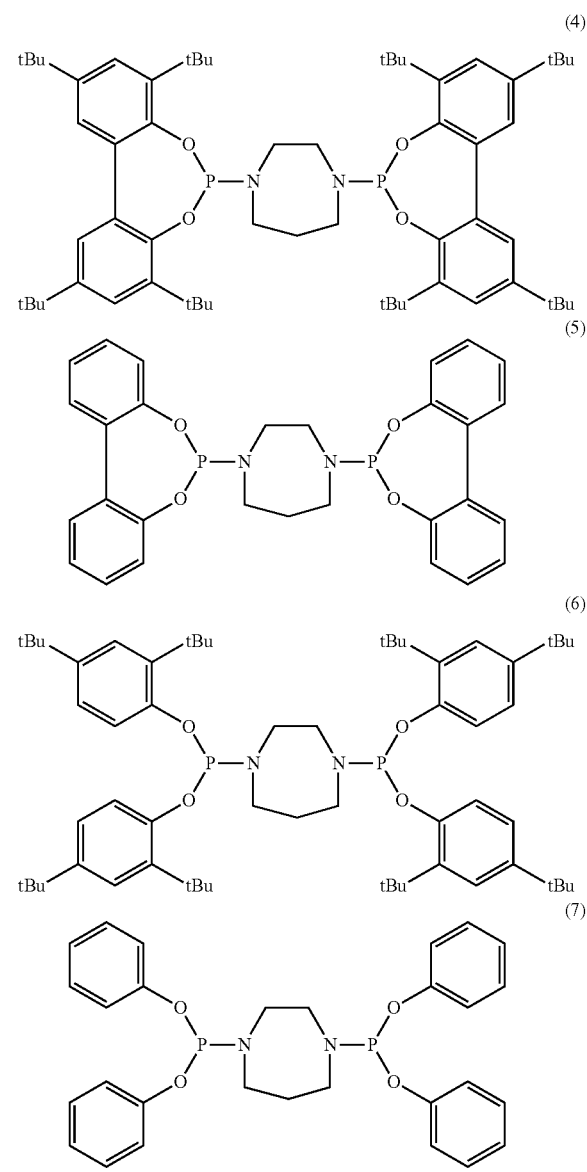

The invention also relates to a complex comprising Rh, Ru, Co or Ir and an above-described inventive compound of one of the formulae (I) and (II).

The complexes according to the invention are suitable as catalysts for the hydroformylation of olefins, for example of octenes or pentene, with which high yields can be achieved. In addition, through suitable selection of the catalysts, it is possible to control the n/iso ratio.

The catalysts according to the invention feature the inventive compounds of the formulae (I) and (II), which have not been used to date in the hydroformylation of olefins.

Rhodium complexes are particularly suitable catalysts for hydroformylation. Preferably, the catalysts according to the invention therefore comprise Rh.

In one embodiment, the complexes are a complex of the formula 8 or 9:

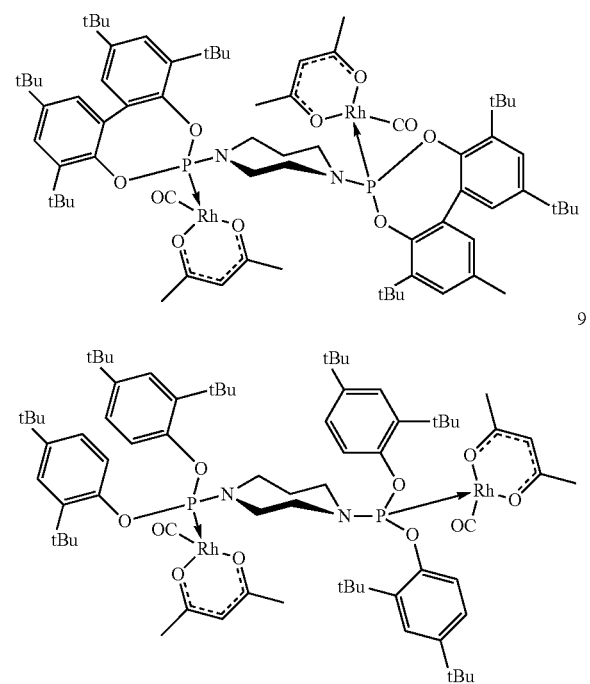

The invention also relates to the use of the complex according to the invention or of the inventive compounds of one of the formulae (I) and (II) for catalysis of a hydroformylation reaction. More particularly, this relates to the hydroformylation of olefins having 2 to 20 carbon atoms, preferably 2 to 12 carbon atoms, more preferably 4 to 10 carbon atoms.

The invention also relates to a process for preparing an aldehyde, comprising the process steps of:
a) initially charging an olefin,
b) adding a complex according to the invention or an inventive compound of one of the formulae (I) and (II) and a catalyst precursor comprising an Rh, Ru, Co or Ir complex,
c) feeding in hydrogen and carbon monoxide,
d) heating the reaction mixture, with conversion of the olefin to an aldehyde. In this process, process steps a) to d) can be effected in any desired sequence.

The reactants in the process according to the invention are olefins or mixtures of olefins, especially of olefins having 2 to 20 carbon atoms, preferably 2 to 12 carbon atoms, more preferably 4 to 10 carbon atoms.

Particularly suitable olefins are monoolefins having a terminal carbon-carbon double bond.

Suitable olefins are, for example 1-propene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (dibutene), nonenes, 2- or 3-methyloctenes, the $C_9$ olefin mixture obtained in the trinnerization of propene (tripropene), decenes, 2-ethyl-1-octene, dodecenes, the $C_{12}$ olefin mixture obtained in the tetramerization or the trimerization of butenes (tetrapropene or tributene), tetradecenes, hexadecenes, the $C_{16}$ olefin mixture obtained in the tetramerization of butenes (tetrabutane), and olefin mixtures prepared by cooligomerization of olefins having different numbers of carbon atoms (preferably 2 to 4).

In a preferred variant of the process, the catalyst used is a complex according to the invention comprising Rh.

The catalyst complex can also be formed in situ, by adding, in step b), a compound of one of the formulae (I) and (II) which functions as ligand, and a catalyst precursor comprising an Rh, Ru, Co or Ir complex. A ligand exchange reaction between the ligands of the catalyst precursor and the compound of one of the formulae (I) and (II) forms the catalyst complex according to the invention here.

In this case, it is also possible to use an excess of ligands, such that, after formation of the catalytic complex, not necessarily every ligand is in the form of a ligand-metal complex; instead, a portion of ligands added is present in unbound form in the reaction mixture.

The molar ratio of the compound of one of the formulae (I) and (II) to the metal atom of the catalyst precursor is preferably in the range from 40:1 to 1:1, preferably 20:1 to 1:1, more preferably 5:1 to 1:1.

The catalyst precursor is preferably an Rh, Ru, Co or Ir complex comprising a ligand selected from acetylacetonate (acac), acetate (OAc) and chloride. More preferably, the catalyst precursor is an Rh complex.

Preferably, the catalyst precursor comprises rhodium carbonyls, rhodium nitrate, rhodium chloride, $Rh(CO)_2(acac)$ (acac=acetylacetonate), rhodium acetate or rhodium carboxylates, for example rhodium octanoate, more preferably $Rh(acac)(CO)_2$.

The conversion of the olefin to the aldehyde preferably takes place at a temperature of 80° C. to 200° C., preferably 90° C. to 180° C., more preferably 100° C. to 160° C.

The conversion of the olefin to the aldehyde preferably takes place at a pressure of 1 bar to 300 bar, preferably 15 bar to 250 bar, more preferably 15 bar to 50 bar.

In the context of the invention, the expression "—($C_1$-$C_{12}$)-alkyl" encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of —($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

Halogen as substituent on alkyl or aryl includes fluorine, chlorine, bromine and iodine, particular preference being given to chlorine and fluorine.

All elucidations relating to the expression —($C_1$-$C_{12}$)-alkyl in the aforementioned structures of the selenaphosphites and selenodiaryls according to the invention also apply to the alkyl groups in —O—($C_1$-$C_{12}$)-alkyl, that is, in —($C_1$-$C_{12}$)-alkoxy.

Preference is given to unsubstituted straight-chain or branched —($C_1$-$C_6$)-alkoxy groups.

Substituted —($C_1$-$C_{12}$)-alkyl groups and substituted —($C_1$-$C_{12}$)-alkoxy groups in the aforementioned structures of the selenaphosphites and selenodiaryls may have one or more substituents, depending on their chain length. The substituents are preferably each independently selected from:
—($C_3$-$C_{12}$)-cycloalkyl,    —($C_3$-$C_{12}$)-heterocycloalkyl, —($C_6$-$C_{20}$)-aryl, fluorine, chlorine, cyano, formyl, acyl or alkoxycarbonyl. This definition applies to all substituted alkyl or alkoxy groups of the present invention.

Preference is given to unsubstituted —O—($C_6$-$C_{20}$)— groups.

In the context of the present invention, the expression "—($C_6$-$C_{20}$)-aryl and —($C_6$-$C_{20}$)-aryl-($C_6$-$C_{20}$)-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —($C_6$-$C_{10}$)-aryl and —($C_6$-$C_{10}$)-aryl-($C_6$-$C_{10}$)-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

The invention is further illustrated in detail below by examples without the invention being limited to the working examples.

EXAMPLES

The examples which follow illustrate the invention.
General Methods

All reactions were conducted under an inert atmosphere (5.0 argon) using standard Schlenk methodology. The solvents were dried by conventional methods and distilled under argon. If possible, the reactions were monitored by NMR spectroscopy. The yields reported below are isolated yields; melting points are uncorrected.

NMR spectra were recorded at room temperature with a Bruker AV 300 or AV 400 MHz spectrometer. The chemical shifts are in ppm relative to TMS; solvent signals (dichloromethane, $\delta_H$=5.32 ppm, $\delta_C$=53.8 ppm; tetrahydrofuran $\delta_H$=3.58; 1.73 ppm; $\delta_C$=67.5; 25.37 ppm) were used as secondary reference for $^1$H and $^{13}$C NMR spectroscopy. For the $^{31}$P NMR spectra, external $H_3PO_4$ was used as standard.

The IR spectra were recorded on a Nicolet 380 FT-IR. High-resolution mass spectrometry (HRMS) was recorded on an Agilent 6210 E1969A TOF spectrometer. Only the measurements with an average deviation from the theoretical mass of ±2 mDa were considered to be correct.

X-ray diffraction data of single crystals of the compound 9 were recorded on a Bruker APEX II Kappa Duo diffractometer. The structures were solved by direct methods by means of the SHELXS-97 program (G. M. Sheldrick, Acta. Crystallogr. Sect. A. 64 (2008) 112-122) and refined by the full matrix least squares method on $F^2$ by means of the SHELXL-2014 program (G. M. Sheldrick, Acta. Crystallogr. Sect. C. 71 (2015) 3-8).

Gas chromatography was conducted on an HP 5890 Series II using a PONA column (0.5 mm; length 50 m; diameter 0.2 mm). All reactions were monitored by thin layer chromatography (silica gel 60, $F_{254}$, E. Merck KGAG). The solvent systems used (v/v) were: hexane-$CH_2Cl_2$ 1:1 ($A_1$), or 5:1 ($A_2$); hexane-EtOAc 99:1 ($B_1$). Detection was effected by UV fluorescence ($\lambda$=254 nm, $\lambda$=365 nm).

Preparative flash chromatography was conducted by using packed columns (silica gel, RediSep) with a Combi-Flash $R_f$ system (Teledyne ISCO).

Synthesis of the Phosphorochloridites 1-3

The phosphorochloridites 1 (E. Benetskiy, S. Lühr, M. Vilches-Herrera, D. Selent, H. Jiao, L. Domke, K. Dyballa, R. Franke, A. Börner, ACS Catal. 4 (2014) 2130-2136), 2 [V. N. Tsarev, A. A. Kabro, S. K. Moiseev, V. N. Kalinin, O. G. Bondarev, V. A. Davankov, K. N. Gavrilov, Russ. Chem. Bull., Int. Ed. 53 (2004) 814-818; D. J. Frank, A. Franzke, A. Pfaltz, Chem. Eur. J. 19 (2013) 2405-2415; 0. Lot, I. Suisse1, A. Mortreux, F. Agbossou, J. Mol. Catal. A: Chem. 164 (2000) 125-130] and 3 (L. P. J. Burton, U.S. Pat. No. 4,739,000 A (1988)) were prepared according to the literature.

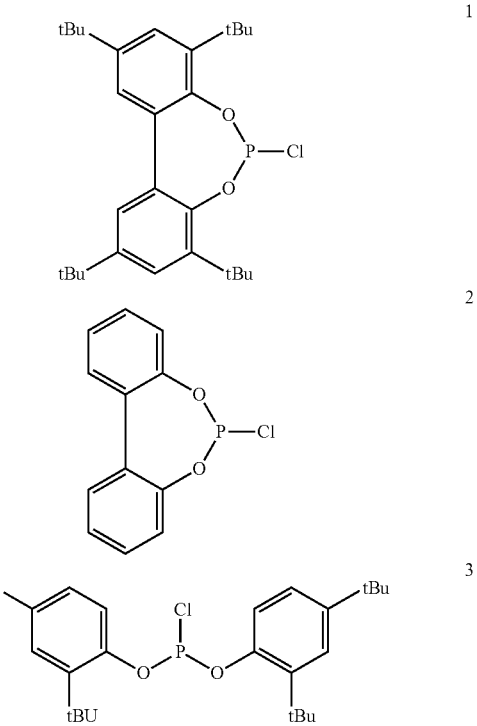

Synthesis of the Phosphoramidites 4, 5 and 6

For general procedure see B. L. Feringa, J. F. Teichert, Angew. Chem. Int. Ed. 49 (2010) 2486-2528; E. Balaraman, K. C. Kumara Swamy, Tetrahedron: Asymmetry 18 (2007) 2037-2048; M. Rodriguez i Zubiri, A. M. Z. Slawin, M. Wainwright, J. Derek Woollins, Polyhedron. 21 (2002) 1729-1736.

A solution of the corresponding phosphorochloridites (2.0 mmol) in THF (20 ml) was added dropwise over a period of 30 min to an ice-cooled solution of the amine (1.0 mmol)

and triethylamine (4.0 mmol) in THF (30 ml). After 15 min, the solution was allowed to warm up gradually to room temperature and the stirring was continued overnight; during this time, triethylammonium hydrochloride precipitated out of the colourless solution and was removable by filtration. After the solvent had been removed under reduced pressure, the crude product was purified by flash chromatography, and it was possible to isolate the amidites as white solids. All ligands are readily available and can be prepared on the gram scale.

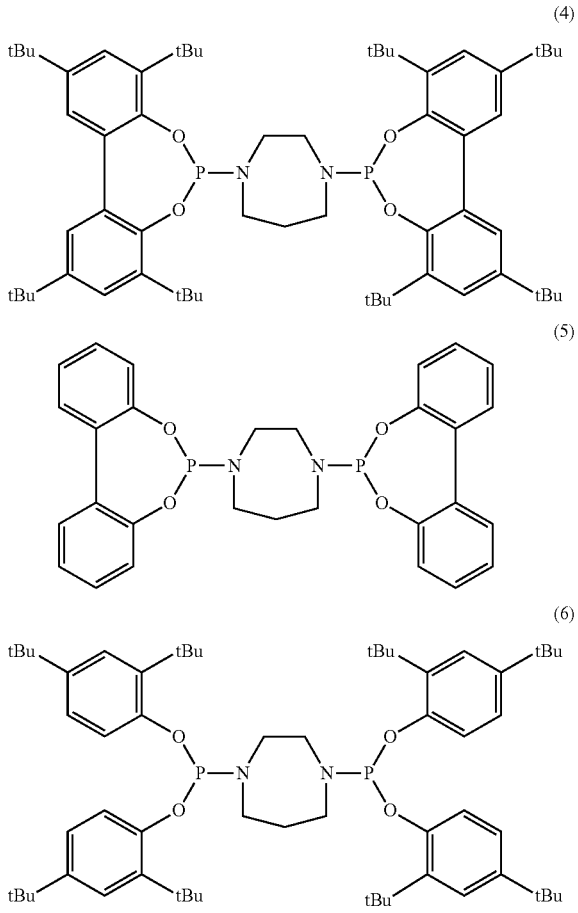

1,4-Bis(2,4,8,10-tetra-tert-butyldibenzo[d,f][1,3,2]dioxaphosphepin-6-yl)homopiperazine (4)

Yield: 64%; fine white crystals; m.p. 317-319° C. (decomposition); $R_f$ 0.30 ($B_1$ system); $^{31}$P NMR (CD$_2$Cl$_2$): δ 146.9 (br. s, 147.8 shoulder); $^1$H NMR (CD$_2$Cl$_2$; 300.13 MHz): δ 7.44; 7.17 (2 br.s, 8H, ArH); 3.42-2.63 (m, 8H, NCH$_2$); 1.90 (m, 2H, NCH$_2$CH$_2$CH$_2$N); 1.48; 1.37 (2 s, 72H, C(CH$_3$)$_3$); $^{13}$C NMR (CD$_2$Cl$_2$; 75.46 MHz): δ 147.86 (ArC—OP); 146.43; 140.17; 132.83 (ArC—C); 126.48; 124.52 (ArCH); 35.66; 34.86 (C(CH$_3$)$_3$); not detectable (NCH$_2$, NCH$_2$CH$_2$); 31.65; 31.02; 30.99 (C(CH$_3$)$_3$); HRMS (ESI) calc. for [M+H]$^+$ C$_{61}$H$_{90}$N$_2$O$_4$P$_2$: 977.6449; found: 977.6445; calc. for [M+Na]$^+$ C$_{61}$H$_{90}$N$_2$O$_4$P$_2$: 999.6268; found: 999.6269; elemental analysis calc. for C$_{61}$H$_{90}$N$_2$O$_4$P$_2$ (%): C, 74.97; (75.05); H, 9.28; (9.42); N, 2.87; (2.62); P, 6.34; (6.32).

1,4-Bis(dibenzo[d,f][1,3,2]dioxaphosphepin-6-yl)homopiperazine (5)

Yield: 40%; white crystals; m.p. 155-157° C.; $R_f$ 0.39 ($A_1$ system); $^{31}$P NMR (CD$_2$Cl$_2$): δ 149.6; $^1$H NMR (CD$_2$Cl$_2$; 300; 13 MHz): δ 7.47 (dd, 4H, J$_{H,H}$=7.57 Hz; J$_{H,H}$=1.79 Hz; ArH); 7.40-7.34; 7.29-7.18 (2m, 12H, ArH); 3.30-3.24; 3.15-3.08 (2m, 8H, NCH$_2$); 1.71-1.63 (m, 2H, NCH$_2$CH$_2$CH$_2$N); $^{13}$C NMR (CD$_2$Cl$_2$; 75.46 MHz): δ 151.80 (d, $^2$J$_{C,P}$=5.26 Hz; ArC—OP); 131.33 (d, $^3$J$_{C,P}$=3.21 Hz; ArC—C); 130.09; 129.64; 124.95; 122.32 (ArCH); 50.89-50.58 (m, $^2$J$_{C,P}$=19.49 Hz; $^3$J$_{C,P}$=3.90 Hz; NCH$_2$); 46.25 (d, $^2$J$_{C,P}$=21.83 Hz; NCH$_2$CH$_2$); 33.23-33.14 (t, $^3$J$_{C,P}$=3.25 Hz; NCH$_2$CH$_2$); HRMS (ESI) calc. for [M+H]$^+$ C$_{29}$H$_{26}$N$_2$O$_4$P$_2$: 529.1441; found: 529.1439; calc. for [M+Na]$^+$ C$_{29}$H$_{26}$N$_2$O$_4$P$_2$: 551.126; found: 551.126; elemental analysis calc. for C$_{29}$H$_{26}$N$_2$O$_4$P$_2$(%): C, 65.91; (65.86); H, 4.96; (4.83); N, 5.30; (5.44); P, 11.72; (11.76).

Tetrakis(2,4-di-tert-butylphenyl)homopiperazine-1,4-diyl bis(phosphonite) (6)

Yield: 64%; white crystals; m.p. 92-94° C.; $R_f$ 0.45 ($A_2$ system); $^{31}$P NMR (CD$_2$Cl$_2$): δ 137.3; $^1$H NMR (CD$_2$Cl$_2$; 300.13 MHz): δ 7.39 (d, 4H, J$_{H,H}$=2.51 Hz; ArH); 7.09 (qd, 8H, J$_{H,H}$=8.42 Hz; J$_{H,H}$=2.44 Hz; ArH); 3.49-3.43 (m, 8H, NCH$_2$); 1.87 (p, 2H, J$_{H,H}$=12.33 Hz; J$_{H,H}$=6.30 Hz; NCH$_2$CH$_2$CH$_2$N); 1.42; 1.33 (2s, 72H, C(CH$_3$)$_3$); $^{13}$C NMR (CD$_2$Cl$_2$; 75.46 MHz): δ 151.80 (d, $^2$J$_{C,P}$=8.37 Hz; ArC—OP); 144.74 (ArC—C); 138.8 (d, $^3$J$_{C,P}$=2.35 Hz; ArC—C); 124.62; 123.7 (ArCH); 117.85 (d, $^3$J$_{C,P}$=22.26 Hz; ArCH); 51.14-50.78 (m, $^2$J$_{C,P}$=19.49 Hz; $^3$J$_{C,P}$=3.90 Hz; NCH$_2$); 46.03 (d, $^2$J$_{C,P}$=20.53 Hz; NCH$_2$CH$_2$); 35.30; 34.66 (C(CH$_3$)$_3$); 31.95 (t, $^3$J$_{C,P}$=4.56 Hz; NCH$_2$CH$_2$); 31.68; 30.20 (C(CH$_3$)$_3$); HRMS (ESI) calc. for [M+H]$^+$ C$_{61}$H$_{94}$N$_2$O$_4$P$_2$: 981.6762; found: 981.6760; calc. for [M+Na]$^+$ C$_{61}$H$_{94}$N$_2$O$_4$P$_2$: 1003.6581; found: 1003.6591; elemental analysis calc. for C$_{61}$H$_{94}$N$_2$O$_4$P$_2$ (%): C, 74.66; (74.64); H, 9.65; (9.59); N, 2.85; (2.81); P, 6.31; (6.26).

Synthesis of Phosphoramidite (7): General Method

See Y. H. Choi, J. Y. Choi, H. Y. Yang, Y. H. Kim, Tetrahedron: Asymmetry. 13 (2002) 801-804; M. Vuagnoux-d'Augustin, A. Alexakis, Chem. Eur. J. 13 (2007) 9647-9662; S. Lühr, J. Holz, A. Börner, Chem Cat Chem. 3 (2011) 1708-1730.

A solution of the amine (1.0 mmol) and triethylamine (5.0 mmol) in THF (5 ml) is added dropwise to phosphorus trichloride (2.0 mmol) at 0° C. The reaction mixture was left to warm up to room temperature and to stir for a further three hours. The resulting HCl gas was driven out of the reaction vessel using a gentle argon stream. The clear solution was concentrated and dried azeotropically with toluene (three times). The resulting residue was used directly in the next step without further purification. The oily crude product was dissolved in THF (20 ml) and cooled to 0° C. A solution of phenol (4.0 mmol) and triethylamine (5.0 mmol) in THF (5 ml) was then added dropwise to the stirred solution.

The reaction mixture was brought gradually to room temperature and the stirring was continued overnight. The precipitate was filtered off and the solution obtained was concentrated. The crude products were purified by flash chromatography and the pure amidite 7 was obtained as a white solid.

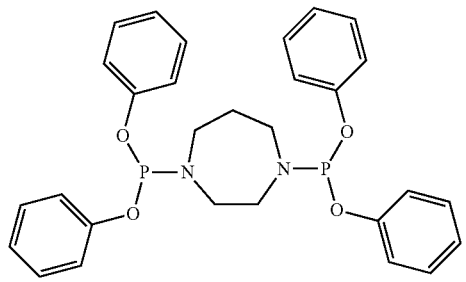

Tetraphenylhomopiperazine-1,4-diyl bis(phosphonite) (7)

Yield: 52%; white crystals; m.p. 51-53° C.; $R_f$ 0.43 ($A_1$ system); $^{31}$P NMR (CD$_2$Cl$_2$): δ 140.50; $^1$H NMR (CD$_2$Cl$_2$; 300.13 MHz): δ 7.37-7.30; 7.14-7.06 (2m, 20H, ArH); 3.47-3.39 (m, 8H, NCH$_2$); 1.91 (p, 2H, J=12.49 Hz; J=6.19 Hz; NCH$_2$CH$_2$); $^{13}$C NMR (CD$_2$Cl$_2$; 75.46 MHz): δ 154.01 (d, $^2J_{C,P}$=6.94 Hz; ArC—OP); 129.99; 123.40; 123.39; 120.33; 120.22 (ArCH); 50.90-50.57 (m, $^2J_{C,P}$=20.47 Hz; $^3J_{C,P}$=4.16 Hz; NCH$_2$); 45.60 (d, $^2J_{C,P}$=20.13 Hz; NCH$_2$CH$_2$); 33.18 (t, $^3J_{C,P}$=3.59 Hz; NCH$_2$CH$_2$); HRMS (ESI) calc. for [M+H]$^+$ C$_{29}$H$_{30}$N$_2$O$_4$P$_2$: 533.17536; found: 533.17594; calc. for [M+Na]$^+$ C$_{29}$H$_{30}$N$_2$O$_4$P$_2$: 555.1573; found: 555.15783; elemental analysis calc. for C$_{29}$H$_{30}$N$_2$O$_4$P$_2$(%): C, 65.41; (65.51); H, 5.68; (5.52); N, 5.26; (5.37); P, 11.63; (11.77).

Synthesis of Rh (I) Complexes 8 and 9

To a solution of Rh(acac)(CO)$_2$ (0.2 mmol) in toluene (5 ml) is added dropwise, at room temperature while stirring, a solution of the ligand (0.1 mmol) in toluene (5 ml) within 10 min. On completion of addition, the reaction solution is stirred for two hours and concentrated under reduced pressure. By washing the residue with hexane (6 ml) and drying at 60° C. over three hours, the spectroscopically pure products are obtained.

FIG. 5. Rh complexes 8 and 9

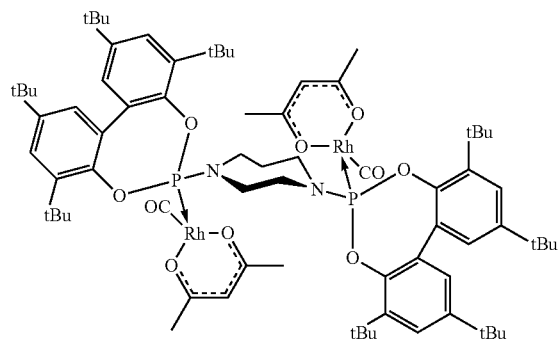

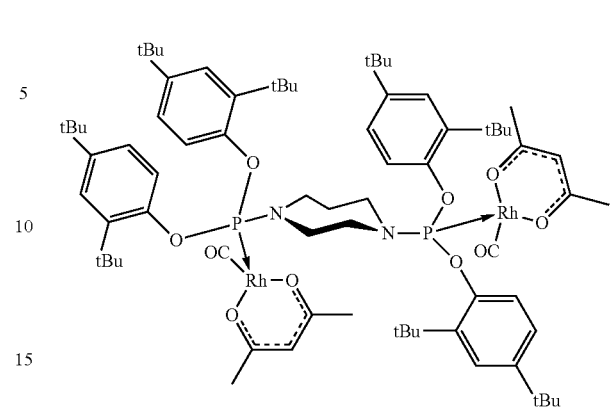

[Rh(Acac)(CO)]$_2$(4) Complex (8)

Yield: quantitative; yellow powder; $^{31}$P NMR (CD$_2$Cl$_2$): δ 146.78 (d, $^1J_{P,Rh}$=279.90 Hz); IR: ν (CO) 2001.3 cm$^{-1}$; $^1$H NMR (CD$_2$Cl$_2$; 300.13 MHz): δ 7.37 (br.d, J$_{H,H}$=2.0 Hz; 4H. ArH); 7.05 (d, J$_{H,H}$=2.36 Hz; 4H, ArH); 5.34 (br. s, 2H, CH$_{acac}$); 4.35-2.33 (m, 8H, NCH$_2$); 1.92 (s, 6H, Me$_{acac}$); 1.68 (br. s, 6H, Me$_{acac}$); not detectable (2H, NCH$_2$CH$_2$); 1.39; 1.25 (2s, 72H, C(CH$_3$)$_3$); $^{13}$C NMR (CD$_2$Cl$_2$; 75.46 MHz): δ 188.17; 184.96 (CO$_{acac}$); 147.5 (ArC—OP); 146.86 (d, J$_{C,P}$=8.4 Hz; ArC—C); 140.51; 131.99; 127.08; 125.21 (ArCH); 101.02 (CH$_{acac}$); not detectable (NCH$_2$, NCH$_2$CH$_2$); 35.88; 34.90 (C(CH$_3$)$_3$); 31.78; 31.56 (C(CH$_3$)$_3$); 27.64 (d, $^5J_{C,Rh}$=7.38 Hz; Me$_{acac}$); 27.46 (Me$_{acac}$); HRMS (ESI) calc. for [M+Na-2H]$^+$ C$_{73}$H$_{104}$N$_2$O$_4$P$_2$Rh$_2$: 1459.51685; found: 1459.51651; elemental analysis calc. for C$_{73}$H$_{106}$N$_2$O$_4$P$_2$Rh$_2$ (%): C, 60.90; (60.92); H, 7.42; (7.32); N, 1.95; (1.91); P, 4.30; (4.54); Rh, 14.30, (14.26).

[Rh(Acac)(CO)]$_2$(6) Complex (9)

Yield: quantitative; yellow powder; $^{31}$P NMR (CD$_2$Cl$_2$): δ 133.35 (d, $^1J_{P,Rh}$=257.25 Hz); IR: ν (CO) 1997.9 cm$^{-1}$; $^1$H NMR (CD$_2$Cl$_2$; 300.13 MHz): δ 7.50 (dd, 4H, J$_{H,H}$=8.52 Hz; 1.62 Hz; ArH); 7.31-7.29 (m, 4H, ArH); 7.04 (dd, 4H, J$_{H,H}$=8.53 Hz, J$_{H,H}$=2.48 Hz, ArH); 5.34 (s, 2H, CH$_{acac}$); 3.72-3.69; 3.61-3.54 (2m, 8H, NCH$_2$); 1.89; 1.41 (2s, 12H, Me$_{acac}$); 1.77 (p, 2H, J$_{H,H}$=12.27 Hz; J$_{H,H}$=6.51 Hz; NCH$_2$CH$_2$); 1.32; 1.23 (2s, 72H, C(CH$_3$)$_3$); $^{13}$C NMR (CD$_2$Cl$_2$; 75.46 MHz): δ 188.17; 185.99 (CO$_{acac}$); 149.61 (d, $^2J_{C,P}$=2.70 Hz, ArC—OP); 145.75 (ArC—C); 138.51 (d, $^3J_{C,P}$=6.0 Hz, ArC—C); 124.66; 123.28 (ArCH); 119.50 (J$_{C,P}$=9.94 Hz; ArCH); 101.07 (CH$_{acac}$); not detectable (NCH$_2$, NCH$_2$CH$_2$); 35.32; 34.72 (C(CH$_3$)$_3$); 31.66; 30.31 (C(CH$_3$)$_3$); 27.56 (d, $^5J_{C,Rh}$=7.06 Hz; Me$_{acac}$); 26.52 (Me$_{acac}$); HRMS (ESI) calc. for [M+Na-2H]$^+$ C$_{73}$H$_{108}$N$_2$O$_{10}$P$_2$Rh$_2$: 1463.54815; found: 1463.54725; elemental analysis calc. for C$_{73}$H$_{110}$N$_2$O$_4$P$_2$Rh$_2$ (%): C, 60.74; (60.78); H, 7.68; (7.69); N, 1.94; (1.82); P, 4.29; (4.32); Rh, 14.26; (14.12).

Hydroformylation Methods

The hydroformylation experiments were conducted in a 200 ml autoclave equipped with a thermocouple, a Bronkhorst HITEC mass flow meter and a Bronkhorst pressure regulator, at 120° C. and a pressure of 50 bar of synthesis gas (99.997%; CO/H$_2$=1:1). The reaction was effected at a constant pressure over a period of four hours. The autoclave together with the storage vessel for the olefin addition was purged repeatedly with argon before the catalyst solution (=metal complex+ligand+solvent) was introduced into the reactor and the olefin to the reservoir vessel (argon countercurrent). In a typical experiment, olefin (15 ml) and catalyst solution (41 ml) were used with an olefin/rhodium ratio of 2000/1. The catalyst solution was heated to the desired reaction temperature under synthesis gas for 30 minutes. After the addition of olefin, the pressure was kept at 50 bar and the gas consumption was measured with a mass flow meter. After four hours, the autoclave was cooled down to room temperature and the pressure was released. The product analysis was effected by gas chromatography; for this purpose, the reaction solution (1 ml) was diluted with n-pentane (10 ml) and toluene was used as internal standard.

Experiments were conducted in each case with n-octenes (EVONIK Industries AG, octene isomer mixture of 1-octene: 3.3%; cis-+trans-2-octene: 48.5%; cis-+trans-3-octene: 29.2%; cis-+trans-4-octene: 16.4%; structurally isomeric octenes: 2.6%), 1-octene or 2-pentene as reactants. The yields and n/iso ratios achieved are shown in Tables 1 to 3. As apparent from the experimental results, the complexes according to the invention are suitable as catalysts for the hydroformylation of olefins, with which virtually quantitative yields can be achieved. Moreover, it is possible via selection of the ligands according to the invention to achieve a high n or iso selectivity.

TABLE 1

Hydroformylation of n-octene with the bidentate diphosphoramidites 4, 5 and 6

| Entry | Ligand | L/Rh | Yield (%) | n selectivity (%) |
|---|---|---|---|---|
| 1 | 4 | 2 | 98.9 | 19.5 |
| 2 | 5 | 2 | 36.8 | 14.4 |
| 3 | 6 | 2 | 95.1 | 18.2 |

TABLE 2

Hydroformylation of 1-octene with the bidentate diphosphoramidites 4 and 7

| Entry | Ligand | L/Rh | Yield (%) | n selectivity (%) |
|---|---|---|---|---|
| 1 | 4 | 2 | 99.6 | 51.8 |
| 2 | 7 | 2 | 85.6 | 68.2 |

TABLE 3

Hydroformylation of 2-pentene with the bidentate diphosphoramidites 5 and 6

| Entry | Ligand | L/Rh | Yield (%) | n selectivity (%) |
|---|---|---|---|---|
| 1 | 5 | 2 | 38.6 | 25.7 |
| 2 | 6 | 2 | 79.5 | 41.0 |

As the results show, the n/iso ratio can be controlled with the aid of the novel ligands.

The invention claimed is:

1. Compound of one of the general formulae (I) and (II)

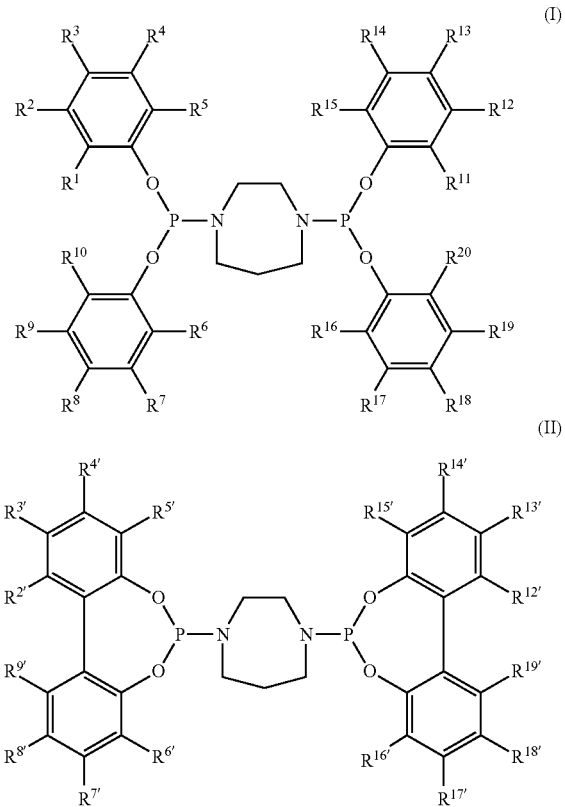

where $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl, halogen, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —OH, —N[$(C_1$-$C_{12})$-alkyl]$_2$;

and $R^{2'}, R^{3'}, R^{4'}, R^{5'}, R^{6'}, R^{7'}, R^{8'}, R^{9'}, R^{12'}, R^{13'}, R^{14'}, R^{15'}, R^{16'}, R^{17'}, R^{18'}, R^{19'}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl, halogen, —COO—$(C_1$-$C_{12})$-alkyl, —CONH—$(C_1$-$C_{12})$-alkyl, —CO—$(C_1$-$C_{12})$-alkyl, —CO—$(C_6$-$C_{20})$-aryl, —COOH, —OH, —N[$(C_1$-$C_{12})$-alkyl]$_2$.

2. Compound according to claim 1, characterized in that $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen.

3. Compound according to claim 1, characterized in that $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl.

4. Compound according to claim 1, characterized in that $R^{2'}, R^{3'}, R^{4'}, R^{5'}, R^{6'}, R^{7'}, R^{8'}, R^{9'}, R^{12'}, R^{13'}, R^{14'}, R^{15'}, R^{16'}, R^{17'}, R^{18'}, R^{19'}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl, -halogen.

5. Compound according to claim 1, characterized in that $R^{2\prime}$, $R^{3\prime}$, $R^{4\prime}$, $R^{5\prime}$, $R^{6\prime}$, $R^{7\prime}$, $R^{8\prime}$, $R^{9\prime}$, $R^{12\prime}$, $R^{13\prime}$, $R^{14\prime}$, $R^{15\prime}$, $R^{16\prime}$, $R^{17\prime}$, $R^{18\prime}$, $R^{19\prime}$ are independently selected from —H, —$(C_1$-$C_{12})$-alkyl, —O—$(C_1$-$C_{12})$-alkyl, —$(C_6$-$C_{20})$-aryl, —O—$(C_6$-$C_{20})$-aryl.

6. Compound according to claim 1, characterized in that $R^1$, $R^2$, $R^4$, $R^7$, $R^9$, $R^{10}$, $R^{11}$, $R^{12}$, $R^{14}$, $R^{17}$, $R^{19}$, $R^{20}$ are each H.

7. Compound according to claim 1, characterized in that $R^{2\prime}$, $R^{4\prime}$, $R^{7\prime}$, $R^{9\prime}$, $R^{12\prime}$, $R^{14\prime}$, $R^{17\prime}$, $R^{19\prime}$ are each H.

8. Compound according to claim 1, characterized in that the compound of one of the formulae (I) and (II) is selected from the compounds (4), (5), (6) and (7)

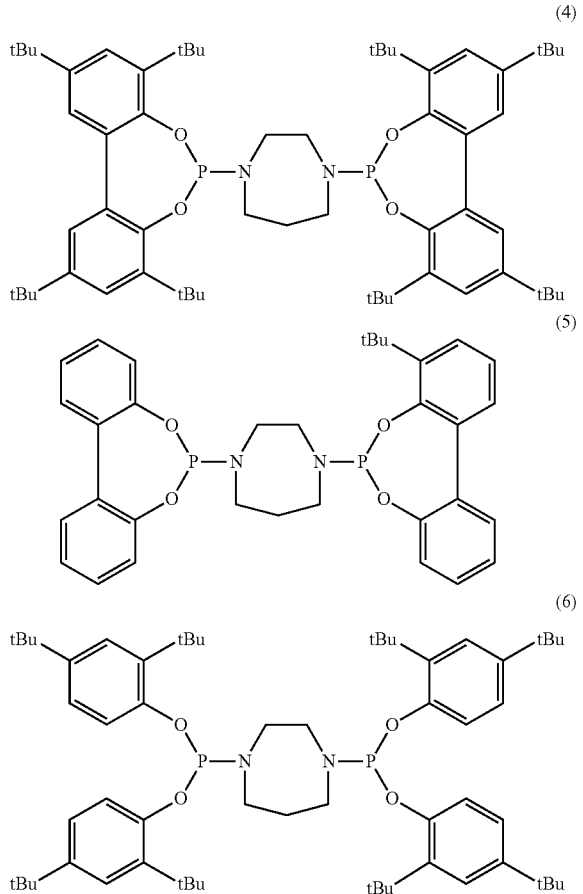
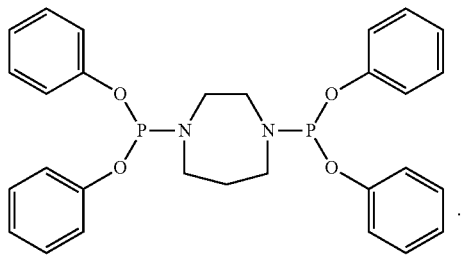

9. Complex comprising Rh, Ru, Co or Ir and a compound according to claim 1.

10. Complex according to claim 9, comprising Rh.

11. A process for hydroformylation, comprising: introducing the compound according to claim 1 as a catalyst.

12. Process for preparing an aldehyde, comprising the process steps of:
 a) initially charging an olefin,
 b) adding a complex according to claim 9 and a catalyst precursor comprising an Rh, Ru, Co or Ir complex,
 c) feeding in hydrogen and carbon monoxide,
 d) heating the reaction mixture, with conversion of the olefin to an aldehyde.

13. Process according to claim 12, characterized in that the catalyst precursor comprises a ligand selected from acetylacetonate, acetate and chloride.

14. Process according to claim 12, characterized in that the catalyst precursor is $Rh(acac)(CO)_2$.

15. A process for hydroformylation, comprising: introducing the complex according to claim 9 as a catalyst.

16. Process for preparing an aldehyde, comprising the process steps of:
 a) initially charging an olefin,
 b) adding a compound according to claim 1 and a catalyst precursor comprising an Rh, Ru, Co or Ir complex,
 c) feeding in hydrogen and carbon monoxide,
 d) heating the reaction mixture, with conversion of the olefin to an aldehyde.

17. Process according to claim 16, characterized in that the catalyst precursor comprises a ligand selected from acetylacetonate, acetate and chloride.

18. Process according to claim 16, characterized in that the catalyst precursor is $Rh(acac)(CO)_2$.

* * * * *